United States Patent [19]

Osterburg

[11] Patent Number: 4,902,385
[45] Date of Patent: Feb. 20, 1990

[54] PROCESS FOR THE PURIFYING DISTILLATION OF CRUDE SEC-BUTYL ALCOHOL

[75] Inventor: Gunther Osterburg, Rheurdt, Fed. Rep. of Germany

[73] Assignee: Deutsche Texaco Aktiengesellschaft, Hamburg, Fed. Rep. of Germany

[21] Appl. No.: 233,775

[22] Filed: Aug. 19, 1988

[30] Foreign Application Priority Data

Aug. 26, 1987 [DE] Fed. Rep. of Germany ....... 3728428

[51] Int. Cl.$^4$ .................. B01D 3/36; C07C 29/82
[52] U.S. Cl. .................................... 203/96; 203/2; 203/18; 203/39; 203/46; 203/83; 203/85; 203/97; 568/895; 568/913
[58] Field of Search .............. 203/96, 97, 92, 93, 203/2, 39, 83, 76, 18, 85, 46; 568/913, 899, 895

[56] References Cited

U.S. PATENT DOCUMENTS

| | | | |
|---|---|---|---|
| 2,788,315 | 4/1957 | Morrell et al. | 203/96 |
| 2,875,138 | 2/1959 | Altreuter et al. | 203/80 |
| 2,915,462 | 12/1959 | Salmon | 203/2 |
| 3,303,108 | 2/1967 | Rauch et al. | 203/96 |
| 3,528,891 | 9/1970 | Rauch et al. | 203/96 |

FOREIGN PATENT DOCUMENTS 829424 3/1960 United Kingdom ............... 568/913
1283435 7/1972 United Kingdom .

*Primary Examiner*—Wilbur Bascomb
*Attorney, Agent, or Firm*—Thomas H. Whaley

[57] ABSTRACT

Practically anhydrous crude sec-butyl alcohol produced by catalytic direct hydration of n-butenes is freed by means of water from the azeotropically boiling and low-boiling by-products by continuous azeotropic distillation in a separation column, the prepurified anhydrous sec-butyl alcohol obtained is withdrawn and the high-boiling by-products are subsequently separated in a separate column.

7 Claims, 5 Drawing Sheets

PROCESS FOR THE PURIFYING DISTILLATION OF CRUDE SEC-BUTYL ALCOHOL

BACKGROUND OF THE INVENTION

The present invention relates to a process for the continuous purifying distillation of crude sec-butyl alcohol, obtained by catalytic hydration of n-butenes at elevated temperature and elevated pressure and by separation of unreacted olefin from the reaction product by feeding the crude alcohol to the upper part of a separation column, supplying the energy required for evaporation in a reboiler at the bottom of the separation column, distilling off overhead the azeotropically and low-boiling by-products in the presence of water and withdrawing the prepurified secbutyl alcohol at the bottom of the separation column and subsequently separating the high-boiling by-products.

DISCLOSURE STATEMENT

DE-PS 24 29 770 discloses a process for the continuous production of lower alcohols by direct catalytic hydration of vaporous lower olefins with liquid water in the presence of acids or strongly acidic solid materials is known, wherein the formed alcohol is withdrawn in vaporous form together with excess reaction gas at the top of the reactor, is separated from gaseous residual olefins by partial pressure release and, optionally, by additional cooling and is obtained in the form of a greater than 80 percent alcohol. According to this process, the alcohol can be obtained both by intermediate pressure release in a separator system and by separation in a pressurized column operating in the known way. In either case, a sec-butyl alcohol containing 15 percent to maximum 23 percent water is obtained.

DE-PS 30 40 997 discloses a process for the continuous production of substantially anhydrous sec-butyl alcohol by catalytic hydration of n-butenes in the presence of a strongly acidic cation exchange resin as catalyst, wherein the reaction product removed in vaporous form at the top of the reactor is liquefied in a pressure range of 2 to 60 bar and at temperatures of maximum 135° C. The water contained in the reaction product is separated in a separator, the liquid mixture of alcohol and residual gas is vaporized and is split in a pressurized column at a pressure of 3 to 30 bar and dry sec-butyl alcohol with less than 0.1 percent water is obtained.

SUMMARY OF THE INVENTION

Applicants provide a process for the continuous purifying distillation of crude sec-butyl alcohol (SBA) obtained by catalytic hydration of n-butenes at elevated temperature and elevated pressure and by separation of unreacted olefin from the reaction product, by feeding the crude alcohol to the upper part of a separation column, supplying the energy required for evaporation in a reboiler at the bottom of the separation column, distilling off overhead the azeotropically and low-boiling by-products in the presence of water and withdrawing the prepurified sec-butyl alcohol at the bottom of the separation column and, subsequently, separating the high-boiling by-products. The process comprises:

(a) feeding for the purification of practically anhydrous crude alcohol the amount of water required for the azeotropic composition of the overhead product obtained to the top tray of the separation column and, by maintaining the temperature between 87.5° C. and 99.5° C. on a middle temperature-controlling tray of the separation column, leading the water feed in the separation column down to this temperature-controlling tray;

(b) feeding the crude alcohol to a feed tray shortly below the top of the separation column;

(c) stripping azeotropically the non-polar by-products boiling at low temperatures as ternary azeotropes with SBA and water by extractive distillation in the water-containing part of the column between the feed tray and the temperature-controlling tray;

(d) stripping at the same time in the water-free part of the column between the temperature-controlling tray and the bottom of the column the polar by-products the separation of which is hampered due to the use of water from the sec-butyl alcohol;

(e) concentrating said by-products together by rectification in the column section between feed tray and top;

(f) condensing the distillation product obtained overhead and returning in a single stream via a reflux drum, the two phases obtained directly from the bottom of the reflux drum to the top tray of the separation column and withdrawing only the increment in light upper phase that is due to the distillation of the crude alcohol as a by-products stream;

(g) complementing by fresh water the water quantity required for maintaining the desired azeotropic composition of the overhead product and removed in the by-products stream; and (h) feeding the fresh water together with the two-phase reflux to the top tray of the separation column while the fresh water feed is controlled by the temperature at the top of the separation column.

DETAILED DESCRIPTION OF THE INVENTION

For the development of a distillation process for the purification of a crude synthesis product, the type, quantity and properties of the by-products contained therein, as well as the purity requirements made on the main product to be produced and the efficiency of the separation steps, are important. For a sec-butyl alcohol (SBA) that is predominantly used for producing methyl ethyl ketone (MEK) by catalytic dehydrogenation, the requirement for purity of the alcohol, particularly in connection with effects in the synthesis or distillation of MEK, has to be fulfilled.

The type of by-products contained in a sec-butyl alcohol produced by catalytic hydration of n-butenes in the presence of strongly acidic cation exchange resins is largely identical with those from conventional sec-butyl alcohol synthesis, for instance, those using sulfuric acid. They are formed by synthesis-dependent side and follow-up reactions of n-butenes but also by reaction of typical accompanying materials contained in the synthesis feedstock such as isobutene, propene and 1,3-butadiene.

The considerably lower tendency to oligomerization of n-butenes, as compared to the conventional synthesis, is characteristic of the formation of by-products in the catalytic hydration of n-butenes in the presence of strongly acidic cation exchange resins as catalyst. Normally, only dimeric follow-up products are formed but no higher polymers as in the sulfuric acid process. This is particularly true of the isobutene or propene contained in different amounts in the synthesis feedstock and hydrated preferably to tertbutyl alcohol or isopopyl alcohol.

Furthermore, it is typical of said synthesis that the formation of di-sec-butyl ether is influenced more distinctly by the synthesis conditions and that, therefore, this ether may be obtained in different quantities in the synthesis. Thus, such a crude sec-butyl alcohol may contain varying amounts of tert-butyl alcohol (TBA), isopropyl alcohol (IPA) and di-sec-butyl ether (DSBE) as main by-products.

The products listed below in Table I characterize, by their quantity and by their separation behavior towards sec-butyl alcohol (and also towards MEK as a follow-up product), the by-products in sec-butyl alcohol that are formed in the synthesis and that are decisive for a purification process. In this connection, varying quantities of polar and non-polar by-products are not unimportant for framing a concept of a purification process.

TABLE I

|     |                         | B.P. °C., 1013 mbar |
|-----|-------------------------|---------------------|
| (a) | Di-sec-butyl ether      | 121                 |
| (b) | tert-Butyl alcohol      | 82.5                |
| (c) | Dimeric $C_4$-hydrocarbons | 99–135           |
| (d) | Isopropyl alcohol       | 82.4                |
| (e) | n-Butyl alcohol         | 117.4               |
| (f) | Butene-(2)-ol-(1),      |                     |
|     | cis-crotonic alcohol    | 123.6               |
|     | trans-crotonic alcohol  | 121.2               |
| (g) | $C_8$-alcohol           | 160                 |

With respect to the purity of the sec-butyl alcohol to be produced, the quantitative separation of those by-products is important, in that their presence may impair not only the purity of sec-butyl alcohol but, particularly, the processing to MEK and the purity thereof.

Relevant hereto is:

(a) The separation of di-secbutyl ether as a main by-product from sec-butyl alcohol.

(b) The separation of all staturated and unsaturated $C_8$-hydrocarbons. This is also valid for the higher-boiling octenes which are difficult to separate as well as for the octadienes derivable from 1,3-butadiene and boiling at 136° C. Both product groups which, together with MEK, are azotropically nonvolatile, are converted by hydrogenation into azeotropically volatile substances with MEK during dehydrogenation of sec-butyl alcohol.

(c) The separation of tert-butyl alcohol and isopropyl alcohol which are difficult to separate from MEK or cannot be separated at all.

(d) The separation of n-butyl alcohol which is dehydrogenated to butyraldehyde in the synthesis of MEK and involves thereafter considerable purification problems.

(e) The separation of all products that boil higher than n-butyl alcohol and already small amounts of which result in deactivation of the catalyst for MEK synthesis during dehydrogenation of sec-butyl alcohol in the gaseous phase process.

The select examples in Table II below demonstrate that the formation of azeotropes of sec-butyl alcohol, with a number of by-products or of the latter among themselves, is so complicated that certain by-products can only be separated in the form of ternary azeotropes with water.

TABLE II

BINARY AND TERNARY AZEOTROPIC DATA FROM SBA DISTILLATION

| No. | Components A | B | C | Azeotrope, b.p. °C. 1013 mbar | Azeotrope in wt. % A | B | C |
|-----|------|------|------|------|------|------|------|
| 1 | SBA | DSBE | — | 99.0 | 77.0 | 23.0 | — |
| 2 | SBA | DSBE | $H_2O$ | 84.4 | 34.1 | 47.9 | 18.0 |
| 3 | DSBE | — | $H_2O$ | 87.5 | 72.2 | — | 27.8 |
| 4 | SBA | Octene+ | — | 95.4 | 62.5 | 37.5 | — |
| 5 | TBA | Octene+ | — | 81.6 | 90.6 | 9.4 | — |
| 6 | TBA | DSBE | $H_2O$ | 77.9 | 53.7 | 32.3 | 14.0 |
| 7 | TBA | — | $H_2O$ | 79.9 | 88.2 | — | 11.8 |

+octene = 3,4-dimethyl-hexene-(2), b.p. °C. 114° C.

According to the prior art, aqueous crude alcohols from conventional hydration processes are first freed by distillation from those substances that are volatile under these conditions by using the water contained therein, before the water is separated from sec-butyl alcohol and the dry sec-butyl alcohol is separated from the remaining higher-boiling impurities.

For instance, in a process that has been performed for decades on a commercial scale, the crude sec-butyl alcohol which contains 30 to 50 percent water after it is stripped from sulfuric acid, is diluted with water before those products with lower boiling points than sec-butyl alcohol or azeotropically lower-boiling product mixtures are distilled off from this dilute alcohol in a so-called prepurifying column. This additional dilution of the crude alcohol with water has the effect that, practically by extractive distillation, the relative volatility of the azeotropically boiling by-products is increased as compared to the sec-butyl alcohol dissolved in water and, thus, the separation efficiency in the specified prepurifying stage is intensified.

The separation efficiency increases as the water dilution increases which, for economical reasons, is limited to approximately 90 percent. The dilution with water has the disadvantage that the increase in relative volatility only applies to the separation of by-products which are insoluble in water such as ether and hydrocarbons, whereas the separation of water-soluble and low-boiling by-products, such as isopropyl alcohol and tert-butyl alcohol, is partly or wholly prevented.

Furthermore, this measure has the disadvantage that the great amount of water required has to be separated again from sec-butyl alcohol in two separation stages, in an azeotrope-formation column and in a dewatering column. Only after this step can the low-boiling, water-soluble by-products be distilled off from dry sec-butyl alcohol in the fourth distillation column, before those by-products that have higher boiling points than sec-butyl alcohol and do not boil azeotropically are separated as high-boiling components in the fifth and final distillation stage.

It becomes apparent from this simplified description that the main problem in the purifying distillation of sec-butyl alcohol is to find a practicable solution for the separation of light ends, azeotrope-forming components and water.

It is true that processes have been disclosed which have the object of simplifying the distillation process for the purification of sec-butyl alcohol but in those processes, aqueous crude alcohol is used.

For instance, in the process described in DE-AS 1 017 602 from the year 1955 which is identical to US-PS 28 75 138, only a two-stage distillation for the purification of sec-butyl alcohol is suggested, wherein the crude alcohol first diluted with sufficient water is freed in the first column from low-boiling impurities (including the azeotropically boiling impurities) and water. In the second column, low-boiling impurities are further separated and high-boiling impurities are separated as well, the secbutyl alcohol being removed at the side of the column. This process requires a sufficient amount of water in the crude alcohol feed in order that all impurities and azeotropes boiling below 99.5° C. are distilled off.

One important requirement for the separation of azeotropically boiling impurities, according to said process, is that the amount of sec-butyl alcohol in the overhead product of the first column exceeds the possible ternary composition of the azeotropic mixture.

However, basis the explanations and conditions of the process according to DE-AS 10 17 602, the desired high purity of the sec-butyl alcohol is not attained.

In DE-OS 2 033 707 the purifying distillation of a water-containing sec-butyl alcohol using a single distillation column is described. The principal subject of said publication is based on the teaching of the aforementioned DE-AS 1 017 602 or US-PS 2 875 138. The removal of vaporous sec-butyl alcohol from the lower water-free column section is emphasized as essential for the invention.

In said application, the expert cannot recognize a more economical and, above all, a more efficient process for the purification of sec-butyl alcohol. In the end, the two columns known from DE-AS 1 017 602 were only placed one upon the other without attaining that the vaporous sec-butyl alcohol removed in the lower part of the column is free from heavy ends or that the vaporization of all sec-butyl alcohol required in the second column is avoided. Furthermore, the separation of d-sec-butyl ether from the produced sec-butyl alcohol is insufficient.

In GB-PS 829 424, a distillation process for the purification of water-containing sec-butyl alcohol from a conventional hydration process is described in which like-wise in the first, column 2, the azeotropically boiling by-products are separated together with water and in the second, column 3, the higher-boiling by-products are separated from the sec-butyl alcohol.

As shown in FIG. 1 of the said British patent specification, the process is supplemented by working up the streams of by-products in an extractor 18 and a column 1.

However, the technical improvements in feasibility on column 2, to ensure the complicated formation of the equilibrium required for the separation, are the essential features of that patent specification. The measures described therein to ensure that the thermodynamic equilibrium in column 2 is primarily orientated to the separation of water entrained with the crude alcohol feed. To this end, on the one hand, with a determined energy supply to the reboiler, a determined reflux is led via stream 9, while the crude alcohol feed and, thus, the entrained water is led via stream 4, depending on the temperature on tray 12. The temperature maintained on tray 12 shall ensure that no water reaches the product at the bottom of column 2. On the other hand, by controlled recycling of an organic phase with a high ether content (stream 24) to the crude alcohol feed and of a phase with a high water content (stream 25) to tray 32, depending on the temperature on tray 28, drying-up of the column towards the top shall be prevented.

Hence, a change in the water balance in the column is accepted at least between tray 12 and tray 28. The description of that process does not reveal that all those complicated control mechanisms for establishing the equilibrium in the column can also be considerably influenced by the composition of the overhead product from column 2 and the resulting solubility product in separator 7 and, thus, do not become easier.

Also in that process, the purity of the sec-butyl alcohol obtained must be insufficient. Furthermore, no statements allowing to as the quality of the sec-butyl alcohol are made.

The processes described in the aforementioned publications raise doubts in their expedience or feasibility, as well as in their separation efficiency for attaining the required product purity. Furthermore, on principle, they are unsuitable for the purification of a dry sec-butyl alcohol because of the high water content in the crude alcohol required for the implementation.

Therefore, it is the object of the present invention to find a suitable distillation process for the purification of a sec-butyl alcohol produced by catalytic hydration of n-butenes, particularly in the presence of strongly acidic cation exchange resins, dried by separation of water from the liquefied reaction product, and isolated by separation from the residual gas mixture by vaporization in a pressurized column, without dispensing with the advantage given by the absence of water in the sec-butyl alcohol thus produced.

It was the object to develop a distillation process for the purification of dry crude sec-butyl alcohol providing, on the one hand, a sec-butyl alcohol of customary, good quality and substituting, on the other hand, the old troublesome process or outweighing the disadvantages recognizable in the disclosed processes.

It was clear that due to the similarity of the by-products the laws of nature recognized in the old distillation process are also valid for the purifying distillation of a sec-butyl alcohol from direct hydration. This means that the water used during distillation cannot be dispensed with. However, on the other hand, the water should be used such that three distillation columns required in the old process, namely azeotrope-formation column, dewatering column and light-ends column, can be dispensed with.

According to the present invention the problem of purifying practically anhydrous crude alcohol is solved by feeding, to the top tray of the separation column, the amount of water required for the azeotropic composition of the overhead product obtained and by maintaining the temperature between 87.5° C. and 99.5° C. on a middle tray of the separation column (temperature-controlling tray), leading the water feed in the separation column down to this temperature-controlling tray, feeding the crude alcohol to a tray shortly below the top of the separation column (feed tray), stripping azeotropically the non-polar by-products boiling at low temperatures as ternary azeotropes with SBA and water by extractive distillation in the water-containing part of the column between feed tray and temperature-controlling tray, stripping at the same time in the water-free part of the column between the temperature-controlling tray and the bottom of the column the polar by-products, the separation of which is hampered due to the use of water from the sec-butyl alcohol and by concentrating those by-products together by rectification in the column section between feed tray and top, condensing the distillation product obtained overhead and, returning in a single stream via a reflux drum, the two phases obtained directly from the bottom of the reflux drum to the top tray of the separation column and withdrawing only the increment in light upper phase that is due to the distillation of the crude alcohol as a by-products stream, complementing by fresh water the water quantity required for maintaining the desired azeotropic composition of the overhead product and removed in the by-products stream and feeding the fresh water together with the two-phase reflux to the top tray of the separation column, while the fresh water feed is controlled by the temperature at the top of the separation column.

According to a preferred embodiment of the process of the invention, the reflux drum is designed as a separator such that not only the light phase is removed as a by-products stream and the two-phase distillation product is removed at the light phase/heavy phase interface and is returned to the top tray of the separation column but also, that from the lower part of the drum aqueous phase is withdrawn from which a sec-butyl alcohol/water azeotrope is obtained by azeotropic distillation and is recycled to the separation column. By the controlled removal of water the increased amount of water entrained in the separation column can be offset.

The total amount of trays in the distillation column required for the separation of low-boiling and azeotropically boiling by-products is not determined because the separation precision of the column may also be influenced by the performance of the separating internals, by the reflux load referring to the column output and by the excess of sec-butyl alcohol in the overhead product.

Preferably, the operation is performed with a total of 55 to 125 trays, 5 to 10 trays thereof being arranged as a rectifying part above the feed tray and the other trays being divided into a water-containing stripping section (above the temperature-controlling tray) and a dry stripping section (below the temperature-controlling tray) by maintaining a guide temperature on the temperature-controlling tray. Fewer trays would result in an uneconomically high reflux for which energy is required. If there are too many trays, the technical expenditure will no longer be transformable into a corresponding economic advantage by reflux minimization. The reflux/crude alcohol feed ratio depends on the number of trays and is between 2.6 : 1 for 55 trays and 1.5 : 1 for 125 trays, relative to the volume.

In particular, with the controlled entraining water in the separation column and the resulting composition of the overhead product or with the overhead temperature, a sec-butyl alcohol/di-sec-butyl ether ratio of between 0.7 : 1 and 10 : 1, preferably between 1 : 1 and 2 : 1, is attained.

DRAWINGS

The invention is illustrated by the drawings which are:

The examination of the separation problem, according to the object, led to the following detailed findings:

1. Separation of sec-butyl alcohol from water

Figure 1:
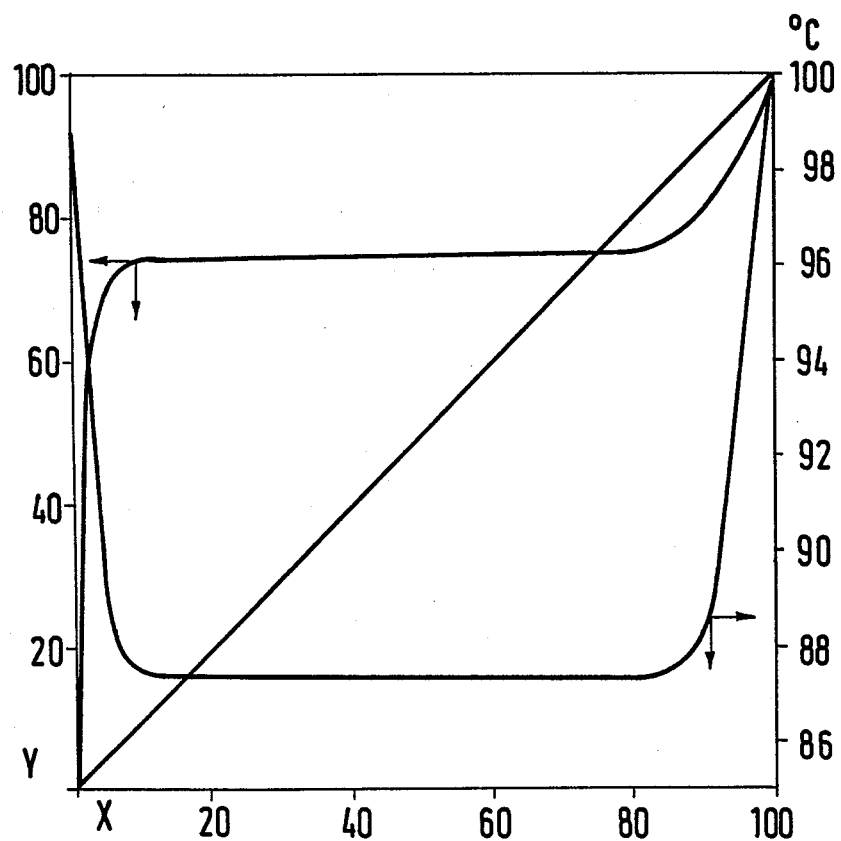
FIG. 1 is a vapor-liquid phase equilibrium of the sec-butyl alcohol/water system.

The vapor/liquid phase equilibrium of the sec-butyl alcohol/water system depicted in FIG.1 with the X-axis=% sec-butyl alcohol in the liquid phase and Y-axis=% sec-butyl alcohol in the vapor phase shows that a separation between dry sec-butyl alcohol and the alcohol/water azeotrope presents few difficulties. During distillation, the transition from azeotrope to dry alcohol takes place in a temperature jump from 87.5° C. to 99.5° C. In a continuous distillation this temperature jump is observed over several trays.

It was found that this temperature jump is suitable for maintaining the concentration equilibrium in the column constant by means of the temperature on a suitable tray in the column and, thus, by temperature-dependent control of the energy supply to the evaporator. A guide temperature of 89° to 91° C. at amospheric pressure has proved particularly suitable. At a guide temperature of e.g. 90° C., a water content of less than 0.1 wt. % in the sec-butyl alcohol is attained, already five trays below the temperature-controlling tray. A stable concentration equilibrium between the azeotropic vapor phase and the water-containing liquid phase is rapidly attained on the distillation trays above the temperature-controlling tray. Thus, it is impossible to attain a water concentration of more than about 20 wt. % in the liquid phases.

With this type of distillation, the total amount of water entrained in the distillation column is separated.

2. Separation of di-sec-butyl ether and dimers

Useful separation of these by-products from sec-butyl alcohol is only feasible as ternary azeotropes with water. The separation of such products becomes more difficult as the boiling points of the products increase because, on the one hand, the amount of products to be separated from the ternary azeotrope with sec-butyl alcohol and water decreases and, on the other hand, the boiling points of the ternary azeotropes gradually approach the boiling point of the binary azeotrope formed by sec-butyl alcohol and water.

Water is not only an auxiliary for the formation of ternary azeotropes but it also favors the separation of these products if it forms a mixture with sec-butyl alcohol in the liquid phase.

For this reason, according to the prior art, the vapor pressure of sec-butyl alcohol, in the liquid phase of the column, was lowered by high dilution with water thus increasing the volatility of the ternary systems from this liquid phase. Also at the same time, a sufficient number of distillation trays and an appropriate reflux was required for the separation.

If drying of sec-butyl alcohol in the same separation step is desired, the water content in the liquid phases of the stripping section (as already described) has to be limited to about 20 percent. Other appropriate measures have to be taken to make up for the thus reduced separation efficiency of the column (lower relative volatility).

It was found that, to this end, first the vapor quantity in the stripping section has to be increased in proportion to the column throughput by recycling an appropriate amount of overhead product. From an energy standpoint, this increase in the reflux ratio has hardly any importance as compared with the prior art process because the column throughput decreases as there is no water load any more and, thus, the vaporization of the reflux is about the same, referring to sec-butyl alcohol.

Secondly, the separation efficiency of the column can be influenced in proportion to the vapor or reflux by the number of stripping trays on which an alcohol/water system is present.

Thirdly, the separation of ether and dimers, by keeping the concentration of these products in the column low, can be favored by feeding the crude alcohol near the column top (e.g., 5 to 10 trays below) and by maintaining a certain excess of binary sec-butyl alcohol/water azeotrope in the ternary mixture of the overhead product.

If ether and dimers drop below the water-containing stripping section of the column due to insufficient separation efficiency, these product residues cannot be separated. Accordingly, the sec-butyl alcohol obtained at the bottom of the column is contaminated with these products.

3. Separation of tert-butyl alcohol and isopropyl alcohol

Since the binary azeotropes of TBA/water and IPA/water have different boiling points as compared to the sec-butyl alcohol/water azeotrope (79.9° C. and 80.4° C. versus 87.5° C.), the separation of these two alcohols does not present any particular difficulties.

However, certain parallels to the prior art process have been found in which, due to the high dilution with water, the separation of water-soluble, low-boiling by-products was difficult and was only feasible after drying of the sec-butyl alcohol.

Also, in a column which is suitable for the separation of ether, dimers and water, those low-boiling but water-soluble products were partially entrained with the downward stream in the column through the aqueous separating zone for ether and dimers.

Quantitative separation is only attained by secondary separation from the anhydrous sec-butyl alcohol. As described in US-PS 2 875 139, this may take place in a second column. However, it is advantageous to carry out this secondary separation simultaneously in the first column by an appropriately sized stripping section in the lower dry part of the column after the separation of water.

4. Composition and phase separation of the overhead product from the separation of low-boiling components In the separation of low-boiling and azeotropically low-boiling by-products from sec-butyl alcohol by means of water, the composition of the overhead product to be distilled off is determined, first by the by-products ratio in the crude alcohol produced, second by the sum of binary and ternary azeotropes that may be formed with those by-products and third by the ratio between the water contained in the overhead product and the water fed to the column. On the other hand, this water ratio and the water balance in the column may be considerably affected by the composition of the heterogenous overhead product and the resulting solution equilibrium between the light organic phase and the heavy aqueous phase.

If, for instance, an insufficient amount of water resulting from vaporization predetermined by the amount of azeotropically boiling by-products, is fed to the column, said products will first withdraw an increasing quantity of water from the water-containing stripping section in the column and then break through to the bottom of the column. At the same time, the content of sec-butyl alcohol in the overhead product will decrease. If too much water is fed to the column, 2.6 parts of sec-butyl alcohol per part of excess water are entrained in the overhead product which means undesired additional expenditure in the recovery of the sec-butyl alcohol from the overhead product.

Figure 2:
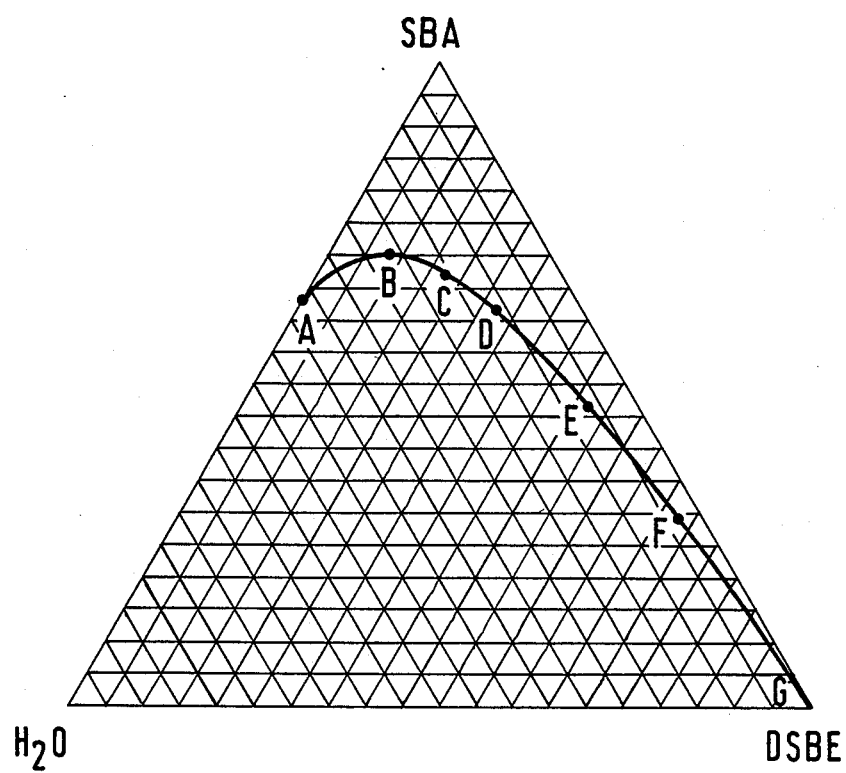
FIG. 2 is a presentation of the solubility proportions in the ternary di-sec-butyl ether/sec-butyl alcohol/water system.

The equilibrium curve A-B-C-D-E-F-G, depicted in FIG. 2, represents the limit of the reciprocal solubility in the system of di-sec-butyl ether (DSBE), sec-butyl alcohol (SBA) and water ($H_2O$). The water content increases and decreases, depending on the concentration of sec-butyl alcohol, so that each change in the ratio of sec-butyl alcohol to di-sec-butyl ether will result in a change in the water concentration.

On the basis of two model examples, the compositions listed below in Table III show possible changes in quantity and concentration during phase separation which result from the compositions of the overhead products. It becomes apparent that the water content in the azeotropic overhead products change less with the SBA content than the water content in the light organic phases resulting therefrom. The amount of heavy aqueous phase that would have to be withdrawn, e.g., when using water-containing crude alcohols, changes to the same extent.

TABLE III

|  | Overhead Product | | Light Phase | | Heavy Phase | |
| --- | --- | --- | --- | --- | --- | --- |
|  | % | Parts | % | Parts | % | Parts |
| Di-sec-Butyl Ether | 40.2 | 474 | 47.4 | 474 | — | — |
| sec-Butyl Alcohol | 39.8 | 470 | 46.0 | 460 | 5.5 | 10 |
| Water | 20.0 | 236 | 6.6 | 66 | 94.5 | 170 |
| Total | 100 | 1,180 | 100 | 1,000 | 100 | 180 |
| Ratio of di-sec butyl ether to sec-butyl alcohol 1:1 | | | | | | |
| Di-sec-Butyl Ether | 25.9 | 300 | 30.0 | 300 | — | — |
| sec-Butyl Alcohol | 52.1 | 605 | 59.0 | 590 | 9 | 15 |
| Water | 22.0 | 255 | 11.0 | 110 | 91 | 145 |
| Total | 100 | 1,160 | 100 | 1,000 | 100 | 160 |

Ratio of di-sec-butyl ether to sec-butyl alcohol 1 : 2

These ratios get yet more complicated if the composition of the azeotropic overhead product is overlapped by the quantities and the ratios of the by-products such as tert-butyl alcohol or isopropyl alcohol to di-sec-butyl ether, as well as to dimeric by-products. Tert-butyl alcohol and isopropyl alcohol increase the water solubility as does sec-butyl alcohol. Dimeric by-products favor the separation of water as does di-sec-butyl ether.

Another interference in the water balance of the column which has to be taken into account is the water quantity phased out, together with varying amounts of byproducts contained in the crude alcohol and with varying compositions of the corresponding parts of the light organic phase.

These procedures and interdependencies, when adjusting the water balance in the column system which are controllable only inadequately and are described in a simplified way, become even more complicated if a constant thermodynamic equilibrium in the separation column is necessary for the separation and only a dry crude alcohol is available as feed to the column.

Technical solutions using the water content in the crude alcohol or the water content in the column as a regulatory means are not applicable to this case.

A process was surprisingly found which offsets the disadvantages of the known processes and allows, even when purifying a dry sec-butyl alcohol, to maintain, in a simple and safe way, the water balance in the column system as desired. To this end, with a reflux adjusted to the requirements of the separation task, practically the total amount of heterogenous overhead product formed is returned from the reflux drum to the top tray of the column, irrespective of its composition and the resulting phase separation. Only the incremental overhead product, resulting from the by-products entrained with the crude alcohol and from the composition of the overhead product, is withdrawn as part of the upper organic phase as overflow from the reflux drum.

To maintain the water balance necessary for the separation and for the composition of the overhead product, the amount of water contained in the withdrawn stream of by-products is continuously complemented by a controlled stream of fresh water fed via a separate line to the reflux drum.

The temperature at the top of the separation column is taken as a regulatory measure for the fresh water feed. It reflects even slight changes in the overhead product composition desired for the separation parameters or in the composition of the resulting organic phase in the reflux drum (see Table IV below).

TABLE IV

| Overhead Product, °C. | 82.3 | 82.6 | 82.8 | 83.4 |
|---|---|---|---|---|
| Water wt. % | 7.6 | 11.0 | 14.6 | 15.9 |
| Dimers wt. % | 6.6 | 7.8 | 4.8 | 3.8 |
| Di-sec-Butyl Ether wt. % | 37.6 | 22.6 | 17.1 | 15.0 |
| tert-Butyl Alcohol wt. % | 18.4 | 20.8 | 27.5 | 24.0 |
| Isopropyl Alcohol wt. % | 1.4 | 0.4 | 1.6 | 1.4 |
| sec-Butyl Alcohol wt. % | 28.4 | 37.4 | 34.4 | 39.9 |
| Ratio of sec-butyl alcohol: di-sec butyl ether | 0.76 | 1.65 | 2.0 | 2.66 |

The following examples illustrate the present invention.

EXAMPLE 1

Figure 3:
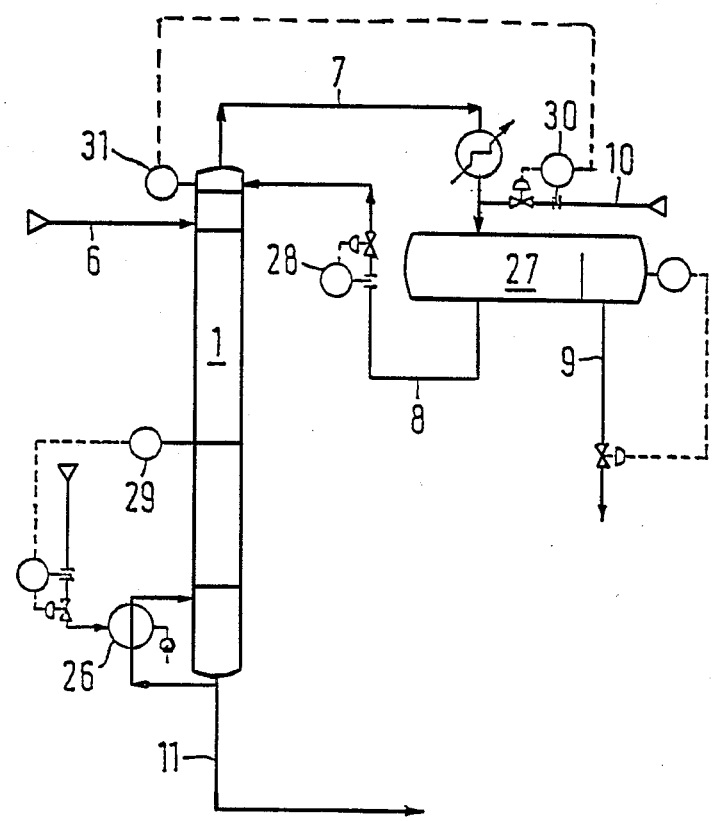
FIG. 3 is a flow sheet of the process according to the invention for the separation of azeotropically and low-boiling impurities of an anhydrous crude sec-butyl alcohol.

The process, according to the invention for the continuous separation of low-boiling and azeotropically boiling by-products from dry crude sec-butyl alcohol, is described in the following with reference to the flow sheet in FIG. 3.

A practically anhydrous crude sec-butyl alcohol from a direct hydration process was continuously fed via line 6 to the 75th tray of a total of 85 practical trays of column 1, i.e., 10 trays below the top of the column. With the choice of tray 75 it was determined that, with feeding the product near the top of the column, most of the separation trays serve the main task of column 1 as a stripping column and only a small part of the separation trays is used for limited rectification.

By addition of water via line 10 to the reflux drum and the separator 27 and from there through line 8, first a sufficient water concentration was attained in the column system which, by means of temperature control 29, allowed to adjust the water quantity on the 35th tray correspondent with a guide temperature of 90° C.±0.5° C., as well as to obtain a water-containing azeotropic overhead product.

The energy required for vaporizing the by-products entrained with the crude alcohol and the reflux introduced into the column through line 8 was fed to reboiler 26, depending on the guide temperature on the 35th tray.

The separating efficiency of column 1 required for attaining the desired alcohol purity was defined, with a total of 85 practical trays, by a rectifying section between the 75th tray and the top of the column, a water-containing stripping section comprising about 40 trays (between the 35th and the 75th tray), a dry stripping section consisting of about 35 trays (between the bottom of the column and the 35th tray), a ratio adjusted thereto of 1.9 parts by volume of reflux from separator 27 to 1.0 part by volume of crude alcohol feed via line 6 and a sufficient excess of sec-butyl alcohol in the overhead product characterized by the secbutyl alcohol/di-sec-butyl ether ratio of 1 : 1 as a minimum and 2 : 1 as a maximum.

With a constant crude alcohol feed, the invariable reflux (stream 8) controlled by valve 28 ensured a relatively steady energy supply to reboiler 26, as well as a smooth temperature control on tray 35 and, thus, constancy of the separation efficiency in the column. The reflux (stream 8) controlled by valve 28 was adjusted, irrespective of the amount of by-products entrained or of the composition of the overhead product (stream 7) or of the resulting phase separation in separator 27, solely to the higher separating efficiency in the stripping section of column 1 desired for this column and triggered by this compulsive reflux.

The azeotropic overhead product obtained after condensation via line 7 in separator 27 corresponds in its quantity to the total organic and aqueous phase entrained with the heterogenous reflux via stream 8 and the amount of by-products entrained with the crude alcohol.

The composition of the azeotropic overhead product and of the organic phase resulting from the phase separation of the overhead product is determined by the amount of water (as aqueous phase and dissolved in the organic phase) entrained in the column with the heterogenous reflux via stream 8 as a function of the amount and the azeotropic properties of the by-products which are entrained with the reflux and the crude alcohol in the column and which are low-boiling under these conditions.

The by-products separated from the crude alcohol were withdrawn as an overflow via line 9 and were led to further processing. They consisted of the light organic phase resulting from the composition of the overhead product.

However, also water was withdrawn via line 9 from the column system. The quantity was determined by the amount of by-products and the water content resulting from the equilibrium in separator 27. By this water removal via line 9 the water deficit gradually increased when dry crude alcohol was fed. Thus, the concentration of sec-butyl alcohol required for this separation or the minimum ratio to di-sec-butyl ether in the overhead product was not reached. Therefore, the water thus removed was complimented by feeding a corresponding water quantity via line 10 and control valve 30 to separator 27 from where it was directly returned with the heterogenous reflux via stream 8 to the top of column 1.

The amount of water fed via control valve 30 must change to the same extent as the amount of by-products entrained with the crude alcohol and/or as the composition of the overhead product and the resulting solution equilibrium in separator 27. As a recognizable measure for the change in quantity on control valve 30 the temperature at the top of the column indicated by temperature gauge 31 is referred to. With a decreasing temperature, referring to the guide temperature, the water quantity was increased via control valve 30, whereas it was lowered with an increasing temperature. The guide temperature and, thus, the composition of the overhead product did not change abruptly because also the total amount of product contained in separator 27 has to adjust in its composition to the overhead product. Modern measuring and control devices allow to control automatically the interdependence between the temperature at the column top and the composition of the overhead product on the one hand and the controlled addition of water on the other.

The validity of the temperature at the top, which corresponds to the desired composition and which can be influenced for a long period without the direct influence of water, solely by the ratio of tert-butyl alcohol or isopropyl alcohol to di-sec-butyl ether or dimers in the crude alcohol, was checked by occasional analysis of the light organic phase in line 9.

At the bottom of column 1 prepurified, dry secbutyl alcohol was withdrawn via line 11 from which the remaining heavy-boiling by-products were separated in a further column and were removed from the bottom of the second column.

Examples for different distillation conditions and the resulting concentrations of by-products in the stripping section of the column or in the purified sec-butyl alcohol withdrawn from the bottom are shown below in Table V.

TABLE V

Influence of the number of trays, the reflux ratio, the concentration of sec-butyl alcohol in the overhead product, and the partition of the stripping section on the concentration of by-products in the lower section of the column

| | Example | | | | | | | | | | |
|---|---|---|---|---|---|---|---|---|---|---|---|
| | 1.1 | 1.2 | 1.3 | 1.4 | 1.5 | 1.6 | 1.7 | 1.8 | 1.9 | 1.10 | 1.11 |
| Total number of trays | 55 | 55 | 55 | 55 | 55 | 55 | 85 | 85 | 85 | 85 | 85 |
| Feed tray | 50 | 50 | 45 | 45 | 45 | 45 | 75 | 75 | 75 | 75 | 75 |
| Temperature-controlling tray | 25 | 25 | 25 | 25 | 25 | 25 | 25 | 25 | 35 | 45 | 45 |
| Crude alcohol feed, l/h | 1.5 | 1.5 | 1.5 | 1.0 | 1.0 | 1.0 | 1.0 | 1.0 | 1.0 | 1.0 | 1.0 |
| Reflux, l/h | 2.6 | 2.6 | 2.6 | 2.6 | 2.6 | 2.6 | 2.1 | 1.9 | 1.9 | 1.9 | 1.7 |
| Reflux/feed ratio | 1.7 | 1.7 | 1.7 | 2.6 | 2.6 | 2.6 | 2.1 | 1.9 | 1.9 | 1.9 | 1.7 |
| SBA/DSBE ratio in the overhead product | 0.7 | 1.9 | 2.5 | 1.5 | 2.3 | 2.8 | 1.9 | 1.9 | 2.0 | 2.0 | 2.0 |
| Crude alcohol, wt. % | | | | | | | | | | | |
| TBA | 0.8 | 1.1 | 1.2 | 1.6 | 2.4 | 2.6 | 1.8 | 1.8 | 1.8 | 1.8 | 1.8 |
| DSBE | 1.3 | 1.2 | 1.1 | 5.9 | 2.6 | 0.9 | 1.3 | 1.3 | 1.3 | 1.3 | 1.3 |
| Tray 47 Crude alcohol, wt. % | | | | | | | | | | | |
| TBA | | | | | | | | | | 0.79 | 1.95 |
| DSBE | | | | | | | | | | <0.001 | <0.001 |
| Tray 42 Crude alcohol, wt. % | | | | | | | | | | | |
| TBA | 9.9 | 3.4 | 1.4 | 0.73 | 1.24 | 1.8 | | | 0.73 | | |
| DSBE | 1.1 | 0.1 | 0.2 | 0.33 | 0.13 | 0.006 | | | <0.001 | | |
| Tray 37 Crude alcohol, wt. % | | | | | | | | | | | |
| TBA | 13.2 | 3.4 | 1.3 | 0.41 | 0.75 | 1.24 | | | 0.35 | | |
| DSBE | 0.6 | 0.03 | 0.04 | 0.05 | 0.02 | 0.002 | | | | | |
| Tray 28 Crude alcohol, wt. % | | | | | | | | | | | |
| TBA | 19.9 | 3.2 | 1.1 | 0.11 | 0.24 | 0.45 | 0.14 | 0.25 | 0.044 | 0.018 | 0.031 |
| DSBE | 0.24 | 0.01 | 0.004 | <0.001 | 0.002 | <0.001 | 0.001 | <0.001 | | | |
| Tray 17 Crude alcohol, wt. % | | | | | | | | | | | |
| TBA | 6.2 | 0.6 | 0.3 | 0.013 | 0.03 | 0.068 | | | | | |
| DSBE | 0.25 | 0.01 | 0.002 | <0.001 | | | | | | | |
| Tray 13 Crude alcohol, wt. % | | | | | | | | | | | |
| TBA | | | | | | | 0.006 | 0.014 | 0.002 | <0.01 | <0.001 |
| DSBE | | | | | | | | | | | |
| Tray 10 Crude alcohol, wt. % | | | | | | | | | | | |
| TBA | 1.8 | 0.13 | 0.06 | 0.002 | 0.004 | 0.009 | | | | | |
| DSBE | 0.23 | 0.01 | 0.001 | | | | | | | | |
| Bottom outlet Crude alcohol, wt. % | | | | | | | | | | | |
| TBA | 0.2 | 0.1 | 0.01 | <0.001 | <0.001 | 0.001 | <0.001 | <0.001 | <0.001 | <0.001 | <0.001 |
| DSBE | 0.2 | 0.01 | 0.001 | <0.001 | <0.001 | <0.001 | <0.001 | <0.001 | <0.001 | <0.001 | <0.001 |

EXAMPLE 2

Figure 4:
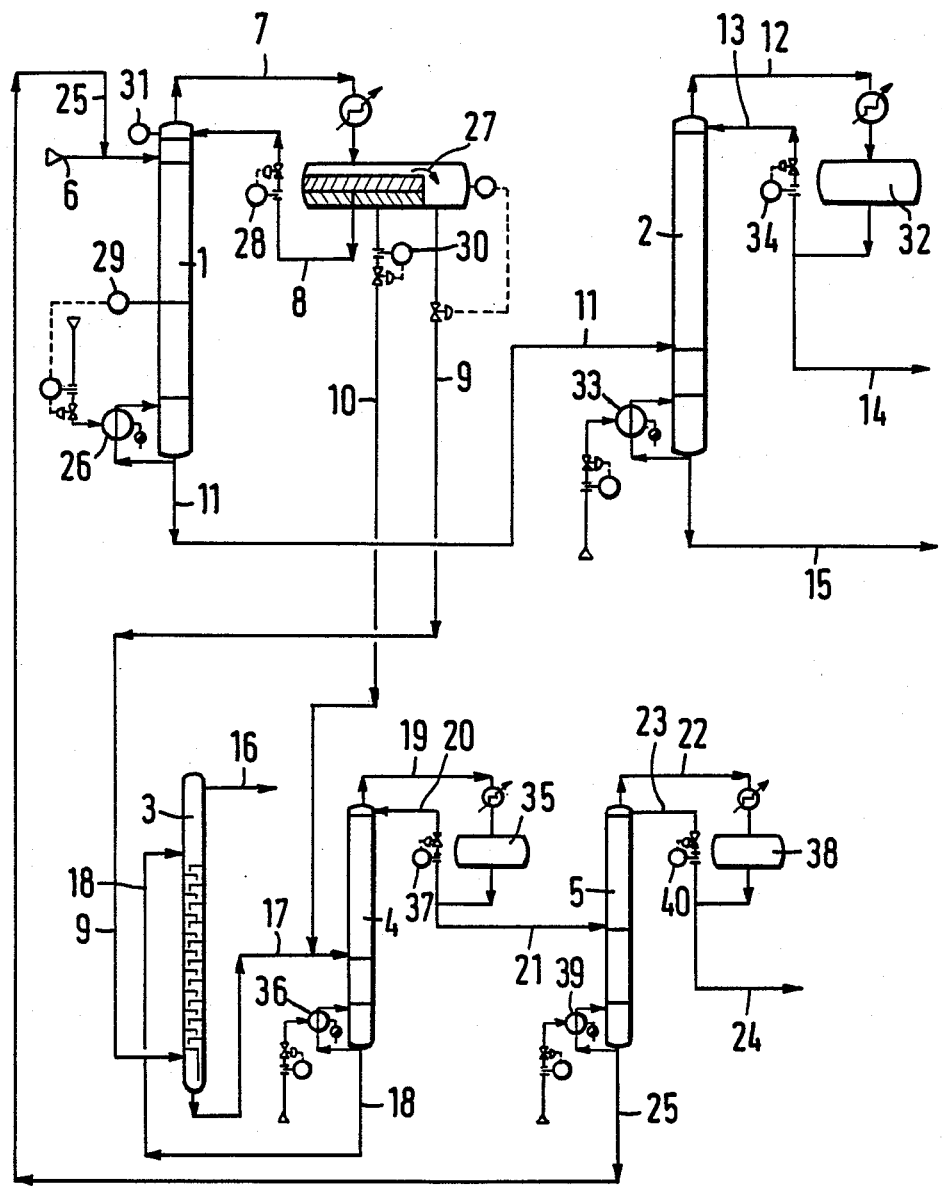
FIG. 4 is a flow sheet of the overall process according to the invention for the purifying distillation of an anhydrous crude sec-butyl alcohol.

According to a further embodiment of the process according to the invention, the entire distillation process for the purification of an anhydrous crude sec-butyl alcohol obtained by hydration of n-butene in the presence of a strongly acidic cation exchange resin as catalyst is illustrated by the flow sheet of FIG. 4.

As in Example 1, the dry crude alcohol was fed via line 6 to purifying distillation but before this stream entered column 1 a water-containing sec-butyl alcohol, obtained as a reflux from the treatment of by-products (from the bottom of column 5), was continuously added. The amount of reflux obtained via line 25 is principally determined by the amount of by-products withdrawn via line 9 from separator 27 and the quantity of sec-butyl alcohol contained therein. The water content in the alcohol/water stream in line 25 was typically about 30 wt. %.

The distillation conditions in column 1 correspond to those in Example 1. The distillation feed from line 6 and line 25 was led to the 75th tray of an 85-tray column. By automatic temperature control on the 35th tray, a water-containing stripping section, comprising about 40 trays, was arranged between the 35th and the 75th tray and the water-free stripping section consisting of about 35 trays was arranged between the bottom of the column and the 35th tray.

The reflux in line 8, adjusted by control valve 28, was 1.9 parts by volume, referring to 1.0 part by volume of crude alcohol feed. The by-products entrained with the crude alcohol and phased out via the overhead product were removed as an azeotropic mixture with sec-butyl alcohol and water via line 9 from separator 27 and were fed to an annex unit for recovering the sec-butyl alcohol contained therein. In extractor 3 of this unit, all water-soluble components, particularly sec-butyl alcohol, tert-butyl alcohol and isopropyl alcohol, were washed out from the by-products stream 9 using the water in line 18 recycled via column 4. All water-insoluble by-products, such as di-sec-butyl ether and dimers were removed from the plant via line 16.

In column 4, the alcohols contained in wash water stream 17 were separated overhead from the water excess as a mixture of the binary azeotropes with water corresponding to the alcohols and were removed via line 21. Sufficient separation between the azeotropes and water was attained by control valve 37 via line 20 with a reflux ratio of about 1 : 1 referring to the stream of line 21.

The azeotropic alcohol/water stream was transferred via line 21 to column 5 and was distilled. The tert-butyl alcohol/water and isopropyl alcohol/water azeotropes, having a lower boiling point than the sec-butyl alcohol/water azeotrope (80° C. vs 87.5° C.), were separated overhead and were removed via line 24. By control valve 40 a sufficient amount of reflux was fed via line 23 to column 5 such that by the resulting separation efficiency of the column the loss of sec-butyl alcohol via line 24, or the recycling of low-boiling by-product alcohols via line 25, could be prevented or kept in the desired limits.

By this measure, the total amount of sec-butyl alcohol withdrawn from separator 27 of column 1 was recycled practically without losses to column 1.

Due to the limited solubility of water which is further reduced by the presence of non-polar by-products, the water content in the stream in line 9 decreased, referring to sec-butyl alcohol, as compared to the stream from line 25 which results from the azeotropic compositions of sec-butyl alcohol and water. Hence, without appropriate measures, the water excess would have snowballed in the system of column 1 because more water in the feed to the column entrains more sec-butyl alcohol in the overhead product and, thus, in the stream of line 9 and, by the recovery of more sec-butyl alcohol, yet more water via line 25 in column 1.

However, in the scope of the process, according to the invention, a simple technical concept was found which allows to adjust and maintain, contrary to Example 1, the water balance in column 1 by continuously controlled removal of water.

Figure 5:
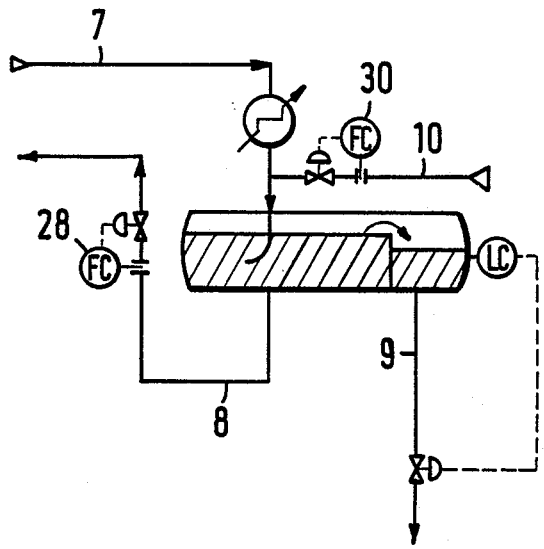
FIG. 5 is a flow sheet of a part of the process with separator according to a first embodiment of the invention.
Figure 6:
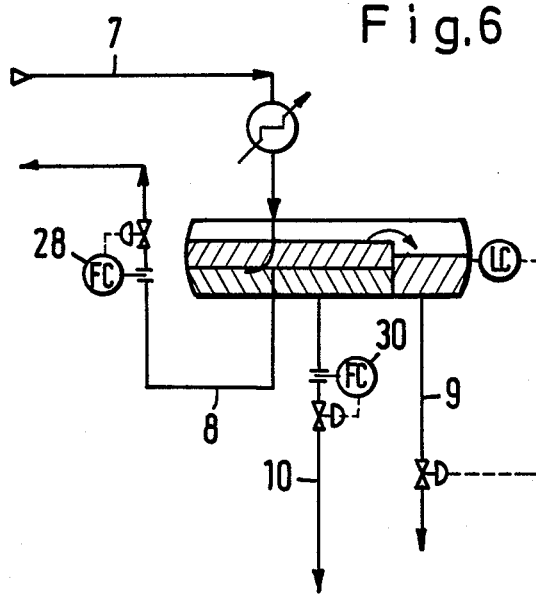
FIG. 6 is a flow sheet of a part of the process with separator according to a second embodiment of the invention.

This technical concept is depicted in a simplified from as shown in FIG. 6 in comparison with the concept of FIG. 5 applied in Example 1.

In FIG. 5 a conventional separator, according to the prior art, is depicted in which , e.g., a cylindrical container is divided into two chambers by a dividing wall, designed as an overflow dam such that the difference of light organic phase between the feed in line 7 and the quantity withdrawing in line 8, forms an overflow from the feeding chamber to the discharge chamber from where it can be withdrawn via line 9.

The separation of heavy phase in the feeding chamber usually desired for a dewatering operation is avoided by the direct removal of light phase from the feeding chamber via line 8 and, thus, the amount of water contained in the stream in line 7 and fed via line 10 is directly recycled to column 1 in the heterogeneous mixture with the light phase.

In the concept depicted in FIG. 6 the line 8 was inserted in the feeding chamber up to about half the height of the overflow dam. Thus, on the one hand, separation and removal of heavy phase with a high content of water is possible. On the other hand, at the interface between heavy and light phase, i.e. on the top edge of the inserted tube, the reflux adjusted on control valve 28 is recycled directly to column 1 in the composition resulting from the difference between the light phase from the feed in line 7 and the overflow to line 9 and from the difference between the heavy phase in the feed, line 7, and the water quantity withdrawn in a controlled way via line 10.

With the controlled water removal via line 10, a higher amount of water entrained in column 1 can be offset with reference to the overhead temperature as an indicator for the desired composition of the overhead product and a sec-butyl alcohol concentration of 1 : 1 to 2 : 1 parts, referring to di-sec-butyl ether preferred for the separation, can be attained. The aqueous stream 10 obtained in the solution equilibrium with the light organic phase contains, among others dissolved sec-butyl alcohol and, for the recovery of this alcohol, is directly fed via line 17 to the feed to azeotropic column 4. The amount of water contained in the stream in line 10 is recycled to column 1 together with the sec-butyl alcohol/water azeotrope via line 21 and the product from the bottom of column 5 via line 25.

The control on control valve 30 influences itself in a reasonable period in that a constant removal of water, via line 10, also causes a constant sec-butyl alcohol concentration in the discharge lines 9 and 10, constant operating conditions in the columns 3 to 5 and a constant water feed via line 25 to column 1.

In the order not to obtain a water deficit in extractor 3 as a result of a great quantity of tert-butyl alcohol or isopropyl alcohol and of the removal of water (about 12%) with the azeotropes via line 24, the wash water in line 18 is complemented accordingly.

The sec-butyl alcohol prepurified as in Example 1 is withdrawn as a dry stream via line 11 at the bottom of column 1 and fed to column 2 in order to separate high-boiling by-products of which the boiling point of N-butyl alcohol (117.8° C.) is the closest to that of secbutyl alcohol (99.5° C.). With the amount withdrawn via line 15 a limited accumulation of high-boiling components at the bottom of column 2 and, thus, in the stream of line 15, may be attained. As a result of this limited accumulation of high-boiling constituents temperature stress and decomposition in the bottom product are avoided and the separation requirements in column 2 as well as the resulting reflux stress via line 13 are lowered. A concentration of n-butyl alcohol of maximum 10 ppm in the pure sec-butyl alcohol obtained via line 14 may be taken as a measure for sufficient separation of high-boiling constituents. This result was obtained with an accumulation of 5 percent high-boiling constituents at the bottom of column 2, with 50 practical trays between the feed via line 11 and the top tray and with a reflux ratio of 0.5.

The amount of sec-butyl alcohol which is contained in the stream in line 15 and which is relatively small with respect to the production can be discarded or can be obtained in distilled form from a separate column, or can be added to the extractor feed (line 9) and, thus, can be recycled without losses via the purifying distillation of by-products. In the latter case, the practically water-insoluble high-boiling by-products are discharged with the ether stream via line 16.

The description of the entire process in Example 2 is supplemented by the compositions of the most important product streams listed below in Table VI.

TABLE VI

| | Components in line | | | | | | |
|---|---|---|---|---|---|---|---|
| | 6 | 9 | 10 | 11 | 14 | 15 | 24 | 25 |
| Water | 0.02 | 11.0 | 89.4 | 0.01 | 0.01 | | 12.0 | 26.2 |
| Dimers | 1.17 | 5.8 | | <0.001 | <0.001 | | | |
| DSBE | 4.73 | 24.1 | | <0.001 | <0.001 | | | |
| TBA | 1.32 | 6.9 | 2.3 | <0.001 | <0.001 | | 87.8 | 2.1 |
| SBA | 92.65 | 52.2 | 8.3 | 99.88 | >99.98 | 93.9 | 0.2 | 71.7 |
| Heavy ends | 0.11 | | | 0.1 | <0.001 | 6.1 | | |

We claim:

1. A process for the continuous purifying distillation of crude sec-butyl alcohol obtained by catalytic hydration of n-butenes at elevated temperature and elevated pressure and by separation of unreacted olefin from the reaction product, wherein the crude sec-butyl alcohol containing di-sec-butyl ether and tertiary butyl alcohol together with higher and lower boiling components is introduced to the upper part of a distillation column, the energy required for distillation is supplied at the bottom of the column, azeotropes formed in the presence of water are distilled of overhead, and dry sec-butyl alcohol is withdrawn at the bottom of the column, said process comprising:
    (a) feeding at the top of the column the amount of water required for forming the azeotropes;
    (b) supplying sufficient energy to the base of the column to maintain a temperature between 87.5° C. and 99.5° C. at a temperature control point in the middle of the column,
    (c) feeding the crude sec-butyl alcohol to the distillation column at a point below the top of the column and above the temperature control point;
    (d) condensing the azeotropes and lower boiling components distilled overhead forming a water rich phase and an alcohol and ether rich phase and returning as reflux to the top of the column the water rich phase and a sufficient amount of the alcohol and ether rich phase to maintain the desired reflux ratio for distillation of all of the azeotropes; and
    (e) withdrawing part of said alcohol and ether rich phase as the top product from the distillation.

2. The process according to claim 1 wherein the separation column contains 55 to 125 trays with 5 to 10 trays thereof above the feed tray as a rectifying section with the remaining other trays functioning as a water-containing stripping section above the temperature control point by maintaining the temperature at the temperature control point within said range.

3. The process according to claim 2 wherein the volume ratio of reflux to the crude alcohol feed ranges from 2.6:1 for a 55 tray column down to 1.5:1 for a 125 tray column.

4. A process according to claim 1 wherein water is supplied to the upper part of the column in a amount sufficient to maintain the ratio of secondary butyl alcohol (SBA) to di-secondary butyl ether (DEBE) at the top of the column in the range of 0.7:1 to 10:1 as determined by the temperature at the top of the column.

5. A process according to claim 4 wherein the amount of water is sufficient to maintain the ratio of secondary butyl alcohol to di-secondary butyl ether in the range of 1:1 to 2:1.

6. A process according to claim 1 wherein the temperature at the temperature control point is within the range of 89° C. and 91° C.

7. A process according to claim 4 wherein the temperature at the top of the column is within the range of 82.3° C. to 83.4° C.

* * * * *